(12) United States Patent
Hluchy

(10) Patent No.: US 11,141,218 B2
(45) Date of Patent: Oct. 12, 2021

(54) BIPOLAR RESECTOSCOPE

(71) Applicant: BOWA-electronic GmbH & Co. KG, Gomaringen (DE)

(72) Inventor: Heinz Hluchy, Moessingen (DE)

(73) Assignee: BOWA-ELECTRONIC GMBH & CO. KG

( * ) Notice: Subject to any disclaimer, the term of this patent is extended or adjusted under 35 U.S.C. 154(b) by 590 days.

(21) Appl. No.: 15/999,567

(22) Filed: Aug. 20, 2018

(65) Prior Publication Data

US 2019/0053844 A1    Feb. 21, 2019

(30) Foreign Application Priority Data

Aug. 18, 2017    (DE) .................... 10 2017 118 885.1

(51) Int. Cl.
| | |
|---|---|
| *A61B 18/14* | (2006.01) |
| *A61B 17/00* | (2006.01) |
| *A61B 18/16* | (2006.01) |
| *A61B 18/00* | (2006.01) |
| *A61B 18/12* | (2006.01) |

(52) U.S. Cl.
CPC ...... *A61B 18/149* (2013.01); *A61B 17/00234* (2013.01); *A61B 18/1445* (2013.01); *A61B 18/16* (2013.01); *A61B 2017/00269* (2013.01); *A61B 2018/00035* (2013.01); *A61B 2018/00077* (2013.01); *A61B 2018/00083* (2013.01); *A61B 2018/00505* (2013.01); *A61B 2018/00601* (2013.01); *A61B 2018/00982* (2013.01); *A61B 2018/126* (2013.01); *A61B 2018/1452* (2013.01); *A61B 2018/1475* (2013.01); *A61B 2018/162* (2013.01)

(58) Field of Classification Search
CPC .......... A61B 17/320016; A61B 18/149; A61B 2018/1407; A61B 2018/141; A61B 2018/144
See application file for complete search history.

(56) References Cited

FOREIGN PATENT DOCUMENTS

| | | |
|---|---|---|
| DE | 25 21 719 | 11/1976 |
| DE | 10 2013 001 156 | 7/2014 |
| EP | 1 163 886 | 5/2006 |
| WO | 2014/114600 | 7/2014 |

OTHER PUBLICATIONS

German Office Action dated Feb. 5, 2018.

*Primary Examiner* — Ronald Hupczey, Jr.
(74) *Attorney, Agent, or Firm* — Gerald E. Hespos; Michael J. Porco; Matthew T. Hespos

(57) ABSTRACT

A bipolar resectoscope (1) has a shaft (2, 2') with an insulating insert (8) at its distal end (7). A working element (3) is mountable in the shaft (2, 2') and a cutting electrode (4) is longitudinally displaceable in the shaft (2, 2'). The insulating insert (8) has an exposed conductive area of a neutral electrode (5, 5'). The area of the passive neutral electrode (5, 5') exposed transverse to the longitudinal axis (34) forms an electrically conductive roof of the insulating insert (8, 8'). An inlet area (26) of the insulating insert (8, 8') has an inner wall (38, 38') with two opposing electrically conductive contact surfaces (39, 39') of the neutral electrode (5, 5') that are parallel to the longitudinal axis (33) and contact two parallel electrically conductive contact tubes (24) of a fork (26) and opening a cutting loop (25) of the cutting electrode (4).

15 Claims, 5 Drawing Sheets

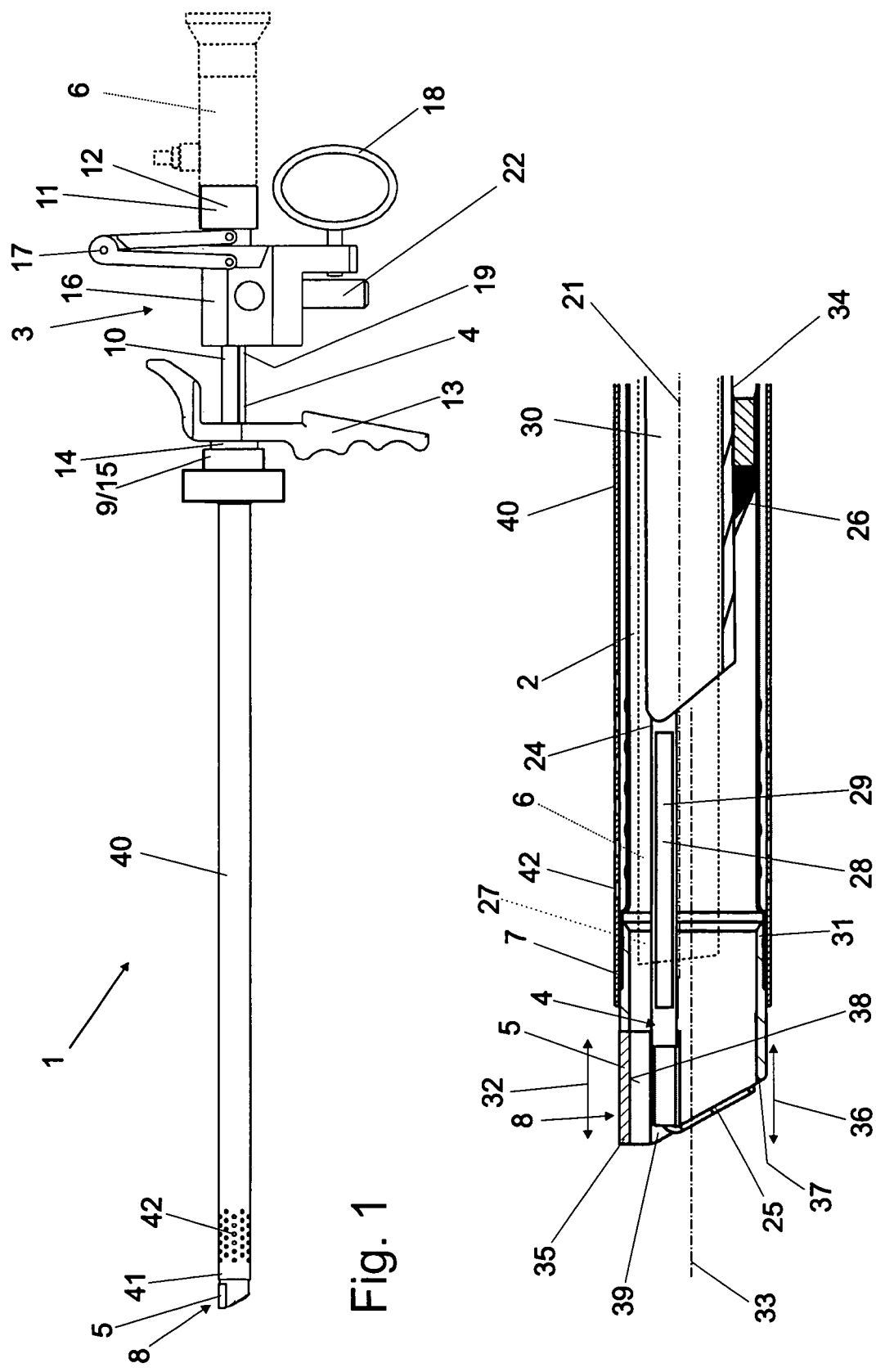

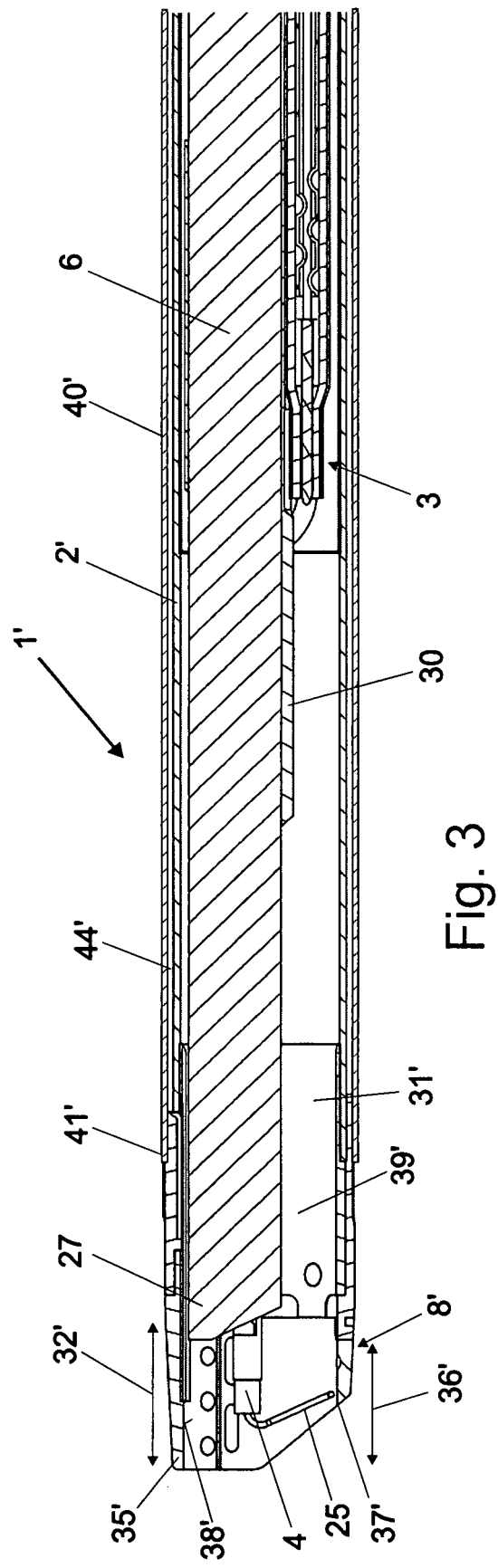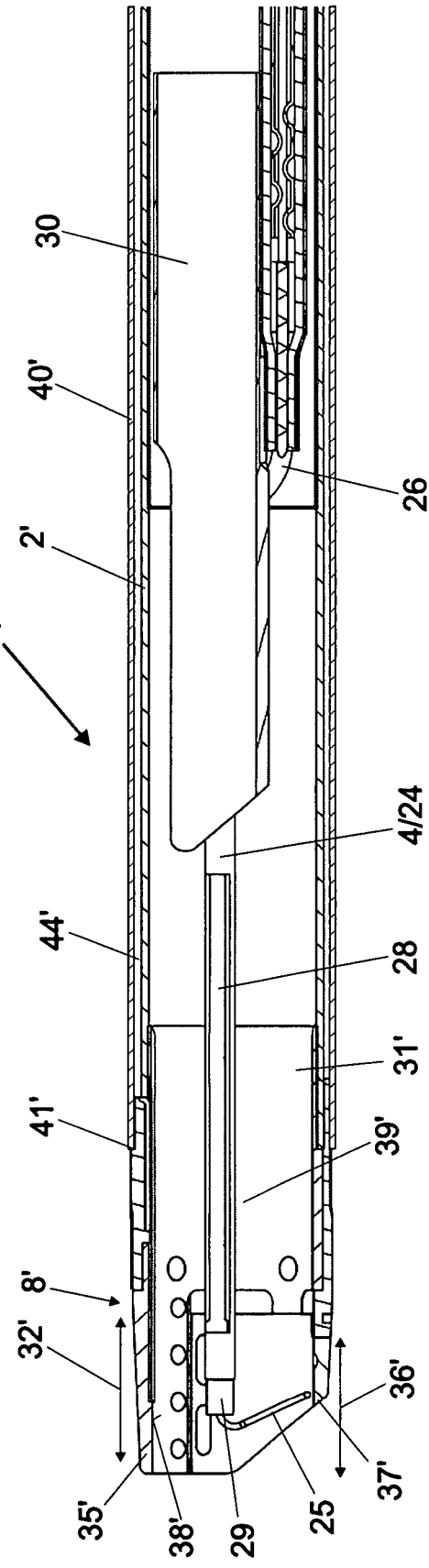

BIPOLAR RESECTOSCOPE

BACKGROUND

Field of the Invention

The invention relates to a bipolar resectoscope, comprising a shaft having an insulating insert made of an electrically non-conductive material at its distal end, where the insulating insert has at its exposed distal end facing away from the shaft an inlet area arranged vertically below the shaft's longitudinal axis for a cutting electrode that can be arranged in a longitudinally displaceable manner inside the shaft. The insulating insert has an exposed electrically conductive area of a neutral electrode that is connected electrically to a passive electrode terminal at the proximal end of the shaft. A longitudinally displaceable working element can be arranged in the shaft in which the active cutting electrode is arranged. The active cutting electrode is connected electrically at its proximal end facing away from the distal end to an active electrode terminal at the proximal end of the working element. The working element has an optical guide tube to accommodate an optical unit that can be inserted into the working element.

Related Art

WO 2014/114600 A1 and its counterpart DE 10 2013 001 156 A1 disclose a bipolar resectoscope is known comprising a shaft which at its distal end has an insulating insert made of an electrically non-conductive material. At its exposed distal end facing away from the shaft and arranged underneath its longitudinal axis, the insulating insert has an inlet area for a cutting electrode that can be arranged in a longitudinally displaceable manner inside the shaft. The insulating insert includes an exposed electrically conductive area of a neutral electrode which is electrically connected to a passive electrode terminal at the proximal end of the shaft. Furthermore, the bipolar resectoscope comprises a working element which can be arranged inside the shaft, and in said working element the active cutting electrode can be arranged in a longitudinally displaceable manner, said active cutting electrode being electrically connected at its proximal end facing away from the distal end to an active electrode terminal at the proximal end of the working element. Finally, the known bipolar resectoscope comprises an optical unit which can be inserted into an optical guide tube of the working element.

According to a first embodiment of the known bipolar resectoscope, its insulating insert comprises an exposed electrode surface as an exposed electrically conductive section of a neutral electrode which is arranged on the inside of the insulating insert radially facing the longitudinal axis thereof and is electrically insulated radially outwards.

The disadvantage here is that the electrode surface is of circumferential configuration, and inside the inlet area of the insulating insert high current density surges can occur on the cutting loop of the active cutting electrode, while the current density is rather too low and has a difficult ignition point for plasma generation when the cutting loop is extended and immersed into the tissue to be sectioned.

According to another embodiment of the known bipolar resectoscope, the exposed electrode surface of the insulating insert is located on the outside radially facing away from the longitudinal axis of the insulating insert and is electrically isolated in inward direction. The disadvantage here is that, on the one hand, the distance between the active cutting electrode's cutting loop in the inlet area and the electrode surface of the neutral electrode is highly variable and requires higher currents, and, on the other hand, that the current density also greatly depends on the positioning of the shaft inside the patient's urethra.

DE 25 21 719 A1 discloses a bipolar resectoscope that also comprises a loop-shaped cutting electrode as active electrode, and the loop-shaped cutting electrode is mounted in a longitudinally displaceable manner by means of a working element in an endoscope shaft. As a passive or neutral electrode between a distal insulating insert and the distal end of an endoscope shaft, an electrically conductive tubular piece is used.

The disadvantage here is that the electrically conductive tubular piece from the distal end of the insulating insert is arranged outside the inlet area to avoid direct contact of the cutting loop of the cutting electrode. This, in connection with the surrounding tissue, depending on the positioning of the shaft in the male urethra, also leads to unwanted varying current densities.

EP 1 163 886 B1 discloses a bipolar resectoscope that comprises a shaft having at its distal end an insulating insert made of an electrically non-conductive material. At its exposed distal end facing away from the shaft and underneath its longitudinal axis, the insulating insert has an inlet area for a cutting electrode that can be arranged in a longitudinally displaceable manner inside the shaft. Furthermore, the bipolar resectoscope comprises a working element that can be arranged in the shaft, and in said working element the active cutting electrode can be arranged in a longitudinally displaceable manner, said active cutting electrode being electrically connected at its proximal end facing away from the distal end to an active electrode terminal at the proximal end of the working element. Finally, the known bipolar resectoscope comprises an optical system which can be inserted into an optical guide tube of the working element. The electrically conductive portion of a neutral electrode of the known bipolar resectoscope is located at the distal end of the active cutting electrode and extends in a roof shape over two bifurcated guide tubes of the active cutting electrode that run parallel to one another.

The disadvantage here is that the surface of the neutral electrode must be relatively large and is extended with the cutting loop, thereby obstructing the field of vision of the optical unit. Furthermore, the line of the neutral electrode must be routed together with the line of the active electrode in the cutting electrode to the proximal end thereof. Depending on the positioning of the resectoscope in the urethra, the extended electrode surface of the neutral electrode can come in contact with surrounding tissue and impact the current flow in an undesirable manner.

The object of the invention is to optimize a generic bipolar resectoscope in such a way that, for one, the passive neutral electrode with a sufficiently large electrode surface is arranged as close to the active cutting electrode as possible, and, secondly, that sufficiently high current densities arise at the cutting loop in connection with the tissue to resect.

SUMMARY

The invention relates to a bipolar resectoscope having a shaft with an insulating insert made of an electrically non-conductive material at its distal end. An exposed distal end of the insulating insert facing away from the shaft has an inlet area arranged vertically below its longitudinal axis and accommodates a longitudinally displaceable cutting electrode. The insulating insert has an exposed electrically conductive area of a neutral electrode that is connected electrically to a passive electrode terminal at the proximal end of the shaft. A working element is mountable in the shaft in which the active cutting electrode is longitudinally displaceable. A proximal end of the active cutting electrode is connected to an active electrode terminal at the proximal end of the working element. The working element has an optical guide tube to accommodate an optical unit that can be inserted in the working element. The area of the passive neutral electrode that is exposed transverse to the longitudinal axis toward the outside forms a consistent electrically conductive roof section in the inward direction of the insulating insert. The roof section is arranged transverse to the longitudinal axis of the insulating insert in vertical direction above the inlet area. The roof section extends over the inlet area of the insulating insert along the longitudinal axis. The inlet area of the insulating insert has an inside wall with two exposed electrically conductive contact surfaces of the neutral electrode that are mounted opposite each other and that run parallel to the longitudinal axis. A cutting electrode may be mounted inside the shaft so that the two exposed electrically conductive contact surfaces of the neutral electrode are in metallic contact respectively with contact tubes of a fork that has two parallel electrically conductive contact tubes. The fork opens a cutting loop of the cutting electrode, and the electrically conductive contact tubes are electrically isolated from the fork.

Due to the fact that the exposed section of the passive neutral electrode forms a continuously electrically conductive roof section of the insulating insert, in particular, the current densities arising in the inlet during tissue resection are more independent of the positioning of the shaft in the male urethra. The exposed portion of the passive neutral electrode being limited to the roof section of the insulating insert, in particular, increases the electrical safety in the inlet area of the insulating insert relative to the cutting loop of the cutting electrode, while further minimizing the dependence of the current density on the positioning of the shaft during resection. The two electrically conductive contact tubes arranged parallel to each other are parts of a fork that opens a cutting loop at the distal end of the cutting electrode with the contact tubes being electrically isolated from the fork.

Given the electrically conductive contact tubes and their electrical contact with the neutral electrode, the contact tubes act as an enlargement of the exposed surface of the neutral electrode so that parts of the exposed electrode surface of the neutral electrode are shifted toward the inside and closer to the active cutting electrode. Independently of the positioning of the longitudinally displaceable cutting electrode, the surface sections of the neutral electrode formed by the contact tubes have the same distance each, since they move with the cutting electrode as a fixed component thereof. Besides improved and more constant current densities, this arrangement also optimizes the ignition point for plasma generation at the beginning of each resection.

The exposed electrically conductive contact surfaces of the neutral electrode on the insulating insert may be formed outside of the roof section and toward the proximal end of the insulating insert by a circumferential contact surface of the neutral electrode that is exposed inwardly. This increases the surface of the passive neutral electrode in the proximal section of the insulating insert without adversely affecting electrical safety.

The electrically conductive contact tubes have longitudinal openings toward an optical unit inserted in the working element and expose the insulating layer below. These longitudinal openings of the contact tubes ensure that an electrically conductive contact is not established with the inserted optical unit in case the electrode is bent due to stress.

The cutting electrode comprises a guide tube in the area of the fork on the distal end of the optical unit inserted in the working element. The guide tube is isolated electrically from the contact tubes and fork. The guide tube of the cutting electrode serves in a manner known per se to stabilize the distal end of the cutting electrode against the optical unit, and, with that, against the shaft. Due to the fact that the guide tube of the cutting electrode is isolated electrically from the contact tubes and the fork, or is made of an electrically non-conductive material. Thus, electrical contact with the optical unit and also with the rest of the instrument is prevented.

The neutral electrode may have an electronically non-conductive coating in its circumference outside of the roof section and the contact surfaces or contact surface, both on its outer and inner surface. To manufacture the insulating insert, it may be easier and more cost-effective to arrange the neutral electrode in a circumferential manner and to apply a non-conductive coating both on its outer and inner surface.

The neutral electrode can also have an electrically non-conductive coating on its front face located outside of the roof section at the distal end of the insulating insert.

In one embodiment, in longitudinal direction, i.e., along the longitudinal axis of the insulating insert, the neutral electrode of the insulating insert is made of a non-conductive material relative to the distal end of the shaft.

At least the inlet area of the insulating insert may be protected by a ceramic coating or a ceramic layer made of zirconium. This increases the endurance of the insulating insert at the cutting edge in the inlet area with respect to the cutting loop.

The insulating insert may be made of a plastic material and the neutral electrode may be made of metal.

In another embodiment, the insulating insert is made of a ceramic material, the neutral electrode is made of a metalized ceramic material.

The shaft may be made of an electrically conductive metal. This is also of advantage in combination with an exterior shaft made of an electrically conductive material.

At least the outer surface of the shaft may be coated with an electrically non-conductive material.

The shaft can be inserted into an outer shaft, thereby creating a suction channel between the outer shaft and the inserted shaft. The outer shaft and the shaft that forms an inner shaft in this case are interlockable in a manner known to a person skilled in the art. The shaft and the outer shaft thus form a so-called continuous flow sheath with continuous flow irrigation in which irrigation fluid is routed via the shaft and aspirated through the suction canal formed between the two shafts.

The distal end of the outer shaft may be recessed relative to the distal end of the insulating insert of the shaft in the proximal area of the insulating insert. In this case, the outer shaft can comprise plural return flow openings at its distal end. However, the return flow openings also can be formed by recesses around the distal end of the shaft that are partially covered by the distal end of the outer shaft.

Further features and advantages of the invention will become apparent from the following specific description and the drawings.

BRIEF DESCRIPTION OF THE DRAWINGS

FIG. 1 is a lateral view of a bipolar resectoscope with the optical unit indicated by dotted lines.

FIG. 2 is a lateral cross-section and magnified view of the distal end of FIG. 1.

FIG. 3 is a lateral cross-section and magnified view of the distal end of a bipolar resectoscope of a second embodiment.

FIG. 4 is a lateral view of the distal end of FIG. 3 without optical unit.

DETAILED DESCRIPTION

Figure 5:
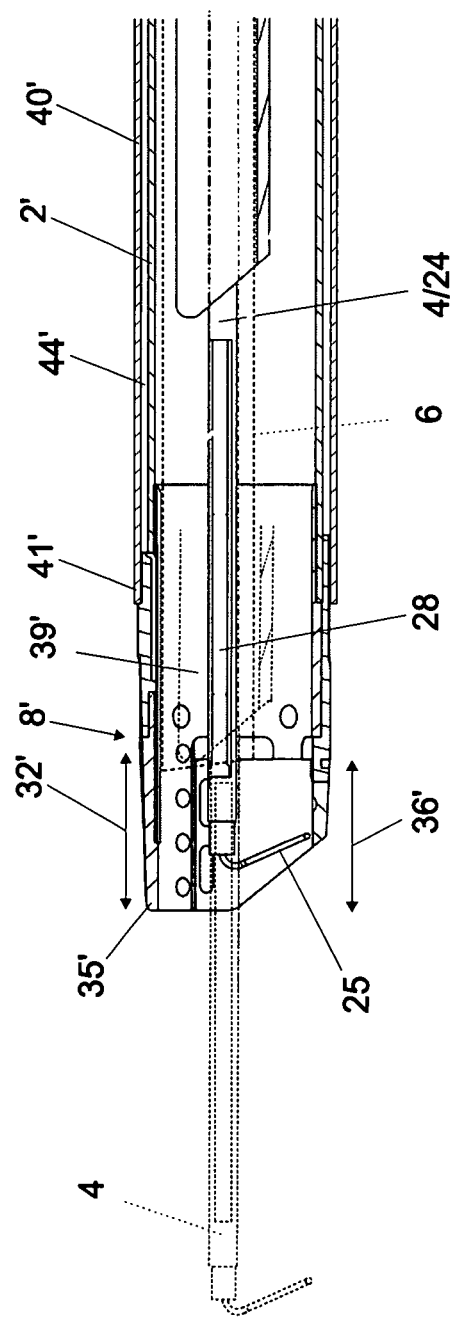
FIG. 5 is a lateral view of the distal end of FIG. 4 with the extended cutting electrode indicated by dotted lines.
Figure 6:
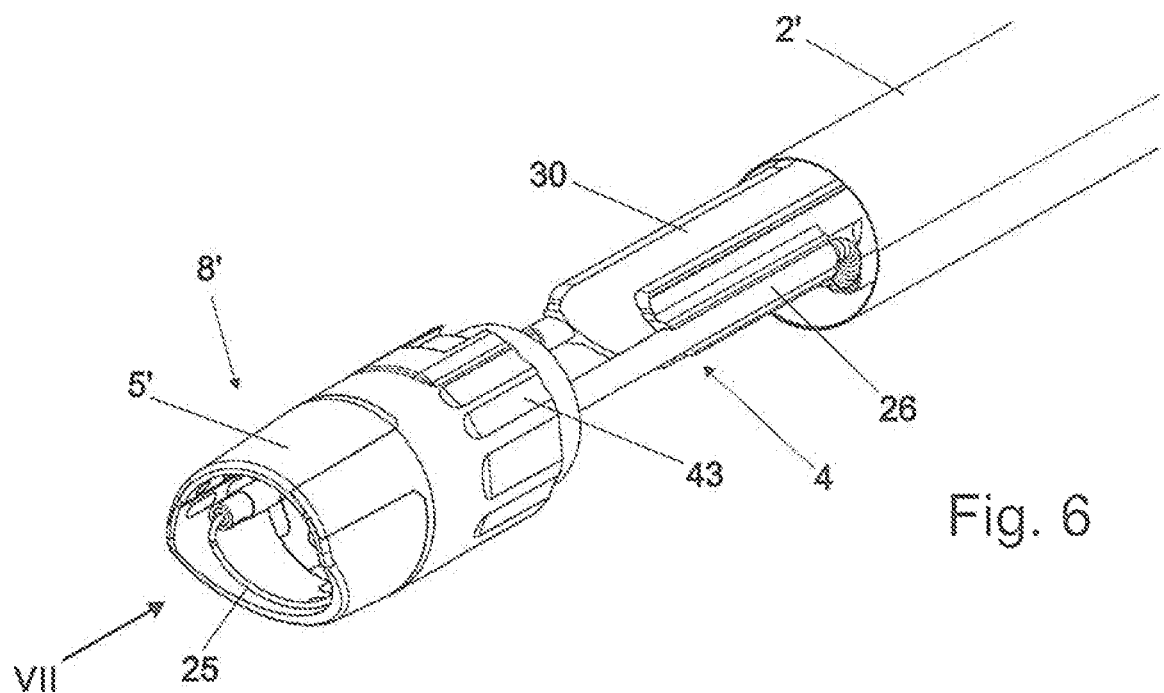
FIG. 6 is a three-dimensional representation of the distal end of FIG. 4, partially sectioned.
Figure 7:
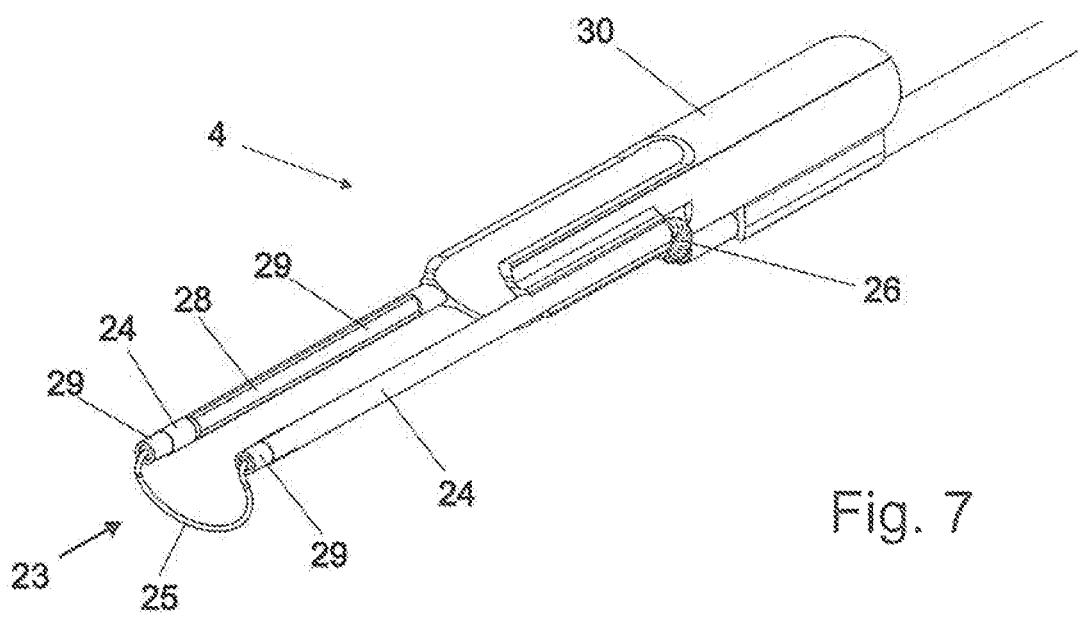
FIG. 7 is a three-dimensional representation of the distal end of the cutting electrode of FIG. 5.
Figure 8:
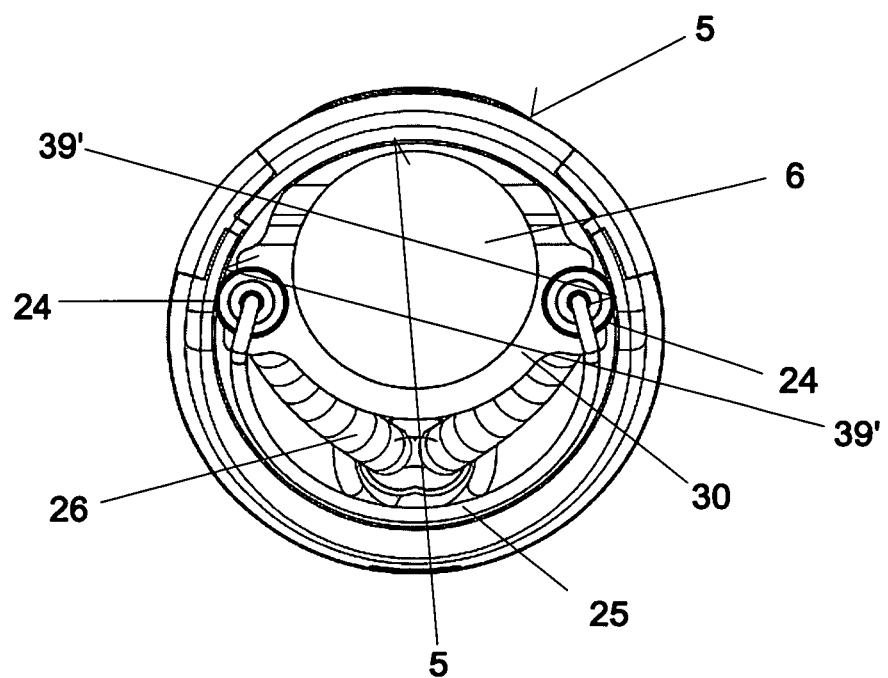
FIG. 8 is a front view of the distal end of FIG. 6 from direction VIII.

A bipolar resectoscope 1 essentially comprises a shaft 2, a working element 3, an active cutting electrode 4, a passive neutral electrode, and an optical unit 6.

At its distal end 7 facing the patient, the shaft 2 has an insulating insert 8. The working element 3 with the cutting electrode 4 can be inserted into the shaft 2 from its proximal end 9 facing away from the distal end 7 and be interlocked with the shaft 2.

The working element 3 has a guide tube 10 on whose proximal end 11 facing the operator a connector 12 is attached to connect an optical unit 6 which is guided inside the optical guide tube 10. The working element 3 comprises a finger grip 13 and an upstream connecting cone 14 in distal direction, in which the working element 3 can be interlocked with a main unit 15 forming the proximal end of the shaft 2.

A longitudinally displaceable sliding body 16 is mounted on the optical guide tube 10. The sliding body 16 is connected to the connector 12 via a resilient hinge 17 and can be pressed by a thumb ring 18 against the spring force of the hinge 17 in the direction of the finger grip 13. The sliding body 16 has a receiving opening to receive a proximal end 19 of the active cutting electrode 4. The sliding body 16 has a guide channel in which the sliding body 16 is guided on the optical guide tube 10, where the longitudinal axis 21 of the optical guide tube 10 aligns with the longitudinal axis of the guide channel 20. Transverse to the longitudinal axis 21, the sliding body 16 has a connector receptacle 22 for a plug (not shown) which, at an instrument-side end of a high frequency cable, can be connected to an active terminal of a high frequency generator (also not shown). Accordingly, the neutral electrode 5 can be connected at its proximal end to a second terminal of the high frequency generator.

The cutting electrode 4 is bifurcated in a manner known per se at its distal end 23 and has two parallel cutting loop guide tubes of a fork 26 arranged almost parallel to the longitudinal axis 21, and between said cutting loop guide tubes a semi-circular cutting loop 25 is opened. According to the invention, the cutting loop guide tubes are configured as electrically conductive contact tubes 24 that are electrically isolated from the fork 26. The contact tubes 24 have one longitudinal opening 28 toward the distal end 27 of the optical unit 6 inserted in the working element 3, said longitudinal opening 28 forming a window which exposes the insulating layer 29 below of the fork 26.

In the area of the fork 26, the cutting electrode 4 has a guide tube 30 along the distal end 27 of the optical unit 6 inserted in the working element 3, said guide tube 30 being electrically isolated from the contact tubes 24 and the fork 26. In particular, the guide tube 30 of the cutting electrode 4 can be made of an electrically non-conductive material.

The insulating insert 8 with its proximal end 31 is fitted at the distal end 7 of the shaft 2, for example via a plug connection, the longitudinal axis 33 of the insulating insert 8 aligning with the longitudinal axis 34 of the shaft 2. On its roof section 32 facing away from the cutting loop 25 in upward and vertical direction, the insulating insert 8 has at its distal end 35 facing away from its proximal end 31 and transverse to the longitudinal axis 33 an area of the neutral electrode 5 that is exposed toward the outside and toward the inside forms the continuously electrically conductive roof section 32 of the insulating insert 8. Facing the roof section 32 in vertical downward direction is an inlet area 36 covered by the roof section 32. The inlet area 36 accommodates a cutting edge 37 over which the cutting loop 25 slides when the cutting electrode 4 is retracted into the shaft 2.

According to the exemplary embodiments in FIGS. 1 and 2, in the inlet area 36 the insulating insert 8 includes on its inside wall 38 two exposed electrically conductive contact surfaces 39 of the neutral electrode 5 opposite each other and parallel to the longitudinal axis 33 which, in a configuration with a cutting electrode 4 mounted inside the shaft 2, are both in metallic contact with the respective adjacent contact tube 24 of the cutting electrode 4.

According to the exemplary embodiments of FIGS. 3 to 5, outside of the roof section 32' toward the proximal end 31' of the insulating insert 8', the insulating insert 8' has a circumferential contact surface 39' of the neutral electrode 5' that is exposed toward the inside. Thus, the contact surface 39' is annular or sleeve-shaped and transitions in distal direction to the area of the neutral electrode 5' in the roof section 32'.

According to the exemplary embodiments of FIGS. 1 to 4, the shaft 2, 2' is arranged in an outer shaft 40, 40' with the two shafts 2, 2' and 40, 40' forming a continuous irrigation shaft with continuous irrigation. The distal end 41, 41' of the outer shaft 40, 40' is recessed from the distal end 35, 35' of the insulating insert 8, 8' in proximal direction in the area of the insulating insert 8, 8'. Between the shaft 2, 2' and the outer shaft 40, 40' a suction channel 44, 44' is formed.

According to FIG. 1, the outer shaft 40 has at its distal end 41 a plurality of return flow openings 42.

According to FIG. 5, the shaft 2' has at its distal end 41' a plurality of groove-like recesses 43' that form inlet openings to the suction channel 44' in connection with the outer shaft 40'.

Of course, the embodiments discussed in the special description and shown in the figures are merely illustrative exemplary embodiments of the present invention. The person skilled in the art is given a wide range of possible variations in view of the present disclosure.

LIST OF REFERENCE NUMBERS 1, 1' Bipolar resectoscope
2, 2' Shaft
3 Working element
4 Cutting electrode
5, 5' Neutral electrode
6 Optical unit
7 Distal end of 2
8, 8' Insulating insert of 2
9 Proximal end of 2
10 Optical guide tube of 3
11 Proximal end of 3
12 Connector of 3

13 Finger grip of 3
14 Connector body of 3
15 Main unit of 2
16 Sliding body of 3
17 Joint of 3
18 Thumb ring of 16
19 Proximal end of 4
20 Guide channel of 16
21 Longitudinal axis of 10
22 Connector receptacle
23 Distal end of 4
24 Contact tube
25 Cutting loop
26 Fork
27 Distal end of 6
28 Longitudinal opening of 24
29 Insulating layer of 26
30 Guide tube of 4
31, 31' Proximal end of 8
32, 32' Roof section of 8
33 Longitudinal axis of 8
34 Longitudinal axis of 2
35, 35' Distal end of 8
36, 36' Inlet area of 8
37, 37' Cutting edge of 8
38, 38' Inside wall of 8
39, 39' Contact surfaces
40, 40' Outer shaft
41, 41' Distal end of 40
42 Return flow openings
43 Recesses of 2
44, 44' Suction channel

What is claimed is:

1. A bipolar resectoscope (1) comprising
a shaft (2, 2') having a distal end (7) and a proximal end (9), a passive electrode terminal disposed at the proximal end (9) of the shaft (2, 2');
a working element (3) mountable in the shaft (2, 2'), the working element having a proximal end (11) with an active electrode terminal, the working element (3) having an optical guide tube (10) to accommodate an optical unit (6) that can be inserted in the working element (3);
an insulating insert (8, 8') made of an electrically non-conductive material being disposed at the distal end (7) of the shaft (2, 2') and having:
a longitudinal axis (33),
a distal end (35, 35') facing away from the shaft (2, 2') and exposed from the shaft (2, 2'), and
an inlet area (36, 36') arranged at the distal end (35, 35') of the insulating insert (8, 8') and disposed below the longitudinal axis (33) of the insulating insert (8, 8') in a vertical direction;
a passive neutral electrode (5, 5') having an exposed electrically conductive area arranged at the distal end (35, 35') of the insulating insert (8, 8'), the passive neutral electrode (5, 5') being electrically connected to the passive electrode terminal at the proximal end (9) of the shaft (2, 2'); and
an active cutting electrode (4) that can be arranged in the working element (3) in a longitudinally displaceable manner, the longitudinally displaceable active cutting electrode (4) having opposite proximal and distal ends (19, 23), the proximal end (19) of the active cutting electrode (4) being connected to the active electrode terminal at the proximal end (11) of the working element (3), the distal end (23) of the active cutting electrode (4) being arranged in the inlet area (36, 36') at the distal end (35, 35') of the insulating insert (8, 8'), the distal end (23) of the active cutting electrode (4) forming a fork (26) having two parallel electrically conductive contact tubes (24) that are electrically isolated from a remainder of the fork (26), the active cutting electrode (4) further having a cutting loop (25) extending distally from the electrically conductive contact tubes (24) wherein:
an area of the passive neutral electrode (5, 5') is exposed toward the longitudinal axis (33) of the insulating insert (8, 8') and forms a roof section (32, 32') of the insulating insert (8, 8'), the roof section (32, 32') being continuously electrically conductive toward the longitudinal axis,
the roof section (32, 32') is disposed offset transversely from the longitudinal axis (33) of the insulating insert (8, 8') in the vertical direction above the inlet area (36) and extends in a direction of the longitudinal axis (33) over the inlet area (36) of the insulating insert (8),
the inlet area (36, 36') of insulating insert (8, 8') has an inside wall (38, 38') with two exposed electrically conductive contact surfaces (39, 39') of the passive neutral electrode (5, 5') facing each other and running parallel to the longitudinal axis (33), the electrically conductive contact surfaces (39, 39') of the passive neutral electrode (5, 5') are respectively in metallic contact with the contact tubes (24) of the fork (26) of the active cutting electrode (4).

2. The bipolar resectoscope of claim 1, wherein
the exposed electrically conductive contact surfaces (39, 39') of the passive neutral electrode (5, 5') of the insulating insert (8, 8') outside of the roof section (32, 32') toward the proximal end (31, 31') of the insulating insert (8, 8') are formed by circumferential contact surfaces (39, 39') of the passive neutral electrode (5, 5') that are exposed toward the inside.

3. The bipolar resectoscope of claim 1, wherein
the electrically conductive contact tubes (24) have longitudinal openings (28) facing an inserted optical unit (6) and exposing an insulating layer (29) below.

4. The bipolar resectoscope of claim 3, wherein
in the area of the fork (26), the cutting electrode (4) has a guide tube (30) that is routed at a distal end (23) of the optical unit (6) inserted in the working element (3) and is electrically isolated from the contact tubes (24) and the fork (26).

5. The bipolar resectoscope of claim 4, wherein
the guide tube (30) of the cutting electrode (4) is made of an electrically non-conductive material.

6. The bipolar resectoscope of claim 1, wherein
a circumference of the neutral electrode (5, 5') outside of the roof section (32, 32') and the contact surfaces (39) or contact surface (39') has an electrically non-conductive coating on both outer and inner surfaces thereof.

7. The bipolar resectoscope of claim 1, wherein
the neutral electrode (5, 5') has an electrically non-conductive coating on a front face thereof located at the distal end (35, 35') of the insulating insert (8, 8') outside of the roof section (32, 32').

8. The bipolar resectoscope of claim 1, wherein
the passive neutral electrode (5, 5') of the insulating insert (8, 8') is non-conductive in longitudinal areas extending to the distal end (35, 35') of the shaft (2, 2').

9. The bipolar resectoscope of claim 1, wherein at least the inlet area (36, 36') of the insulating insert (8, 8') is protected by zirconium dioxide ceramic.

10. The bipolar resectoscope of claim 1, wherein the insulating insert (8, 8') is made of a plastic material and the neutral electrode (5, 5') is made of metal.

11. The bipolar resectoscope of claim 1, the insulating insert (8) is made of a ceramic material and the neutral electrode (5) is made of metalized ceramic.

12. The bipolar resectoscope of claim 1, the shaft (2, 2') is made of an electrically conductive metal.

13. The bipolar resectoscope of claim 1, wherein the shaft (2, 2') is coated with an electrically non-conductive material at least on its outer surface.

14. The bipolar resectoscope of claim 1, the shaft (2, 2') can be inserted into an outer shaft (40, 40') and a suction channel (44, 44') is formed between the outer shaft (40, 40') and the inserted shaft.

15. The bipolar resectoscope of claim 1, wherein the working element (3) has an optical guide tube (10) to accommodate an optical unit (6) that can be inserted in the working element (3).

\* \* \* \* \*